United States Patent
Krauss et al.

(10) Patent No.: US 8,978,344 B2
(45) Date of Patent: Mar. 17, 2015

(54) DEVICE FOR FILLING AND SEALING PHARMACEUTICAL CONTAINERS

(75) Inventors: Ulrich Krauss, Ilshofen (DE); Steffen Humpfer, Satteldorf (DE); Klaus Ullherr, Crailsheim (DE); Werner Mayer, Crailsheim (DE)

(73) Assignee: Robert Bosch GmbH, Stuttgart (DE)

( * ) Notice: Subject to any disclaimer, the term of this patent is extended or adjusted under 35 U.S.C. 154(b) by 615 days.

(21) Appl. No.: 13/378,081

(22) PCT Filed: May 3, 2010

(86) PCT No.: PCT/EP2010/055955
§ 371 (c)(1),
(2), (4) Date: Dec. 14, 2011

(87) PCT Pub. No.: WO2011/000606
PCT Pub. Date: Jan. 6, 2011

(65) Prior Publication Data
US 2012/0090268 A1    Apr. 19, 2012

(30) Foreign Application Priority Data
Jul. 3, 2009  (DE) .......................... 10 2009 027 452

(51) Int. Cl.
*B65B 1/00*    (2006.01)
*B65B 3/00*    (2006.01)
(Continued)

(52) U.S. Cl.
CPC ................. *B65B 3/003* (2013.01); *B65B 7/161* (2013.01); *B65B 7/285* (2013.01); *A61M 5/007* (2013.01)
USPC .......................................................... 53/281

(58) Field of Classification Search
CPC ...... B65B 31/025; B65B 31/02; B65B 3/003; B65B 3/16; B65B 31/028; B65B 5/068; B65B 7/2807; B65D 1/34; B65D 2543/00027; B67B 3/02

USPC .......... 53/432, 471, 485, 488, 489, 510, 511, 53/545, 562, 281

See application file for complete search history.

(56) References Cited

U.S. PATENT DOCUMENTS 3,653,176 A * 4/1972 Gess .................................. 53/64
4,415,085 A * 11/1983 Clarke et al. .................. 206/526
(Continued)

FOREIGN PATENT DOCUMENTS

DE    3819095    12/1989
DE    4419475    12/1995
(Continued)

OTHER PUBLICATIONS

PCT/EP2010/055955 International Search Report, Jan. 6, 2011.

*Primary Examiner* — Robert Long
(74) *Attorney, Agent, or Firm* — Michael Best & Friedrich LLP

(57) ABSTRACT

The invention is a device (10) for filling and sealing pharmaceutical containers. The containers are received in a receptacle (12), in which a carrier element (11) is inserted. The containers are arranged in receivers of the carrier element (11) in multiple rows. The device further includes a first handling unit (27) for removing the carrier element (11) from the receptacle (12), a filling and sealing device (35) for the containers, and a second handling unit (45) for reinserting the carrier element (11) into the receptacle (12) which is conveyed with the carrier element (11) on a conveying device (20). The containers are embodied as syringe barrels (1) or as containers which are to be provided with crimp caps (53), and the second handling device (45) is associated with a crimping device (54).

12 Claims, 3 Drawing Sheets

(51) Int. Cl.
*B65B 5/00* (2006.01)
*B65B 7/16* (2006.01)
*B65B 7/28* (2006.01)
*A61M 5/00* (2006.01)

(56) References Cited

U.S. PATENT DOCUMENTS

| | | | | |
|---|---|---|---|---|
| 4,608,809 | A | * | 9/1986 | Francis et al. .................. 53/471 |
| 4,614,073 | A | * | 9/1986 | Argazzi ............................ 53/54 |
| 4,729,206 | A | * | 3/1988 | Francis et al. .................. 53/297 |
| 5,916,110 | A | * | 6/1999 | Sanfilippo et al. ............. 53/510 |
| 6,164,044 | A | | 12/2000 | Porfano et al. |
| 6,651,404 | B1 | | 11/2003 | Hertfelder |
| 2005/0060962 | A1 | | 3/2005 | Rothbauer et al. |
| 2005/0194059 | A1 | | 9/2005 | Py |
| 2008/0184671 | A1 | | 8/2008 | Fleckenstein et al. |
| 2010/0058711 | A1 | | 3/2010 | Blumenstock et al. |
| 2010/0064631 | A1 | * | 3/2010 | Krauss et al. .................. 53/167 |
| 2010/0180551 | A1 | | 7/2010 | Duethorn et al. |
| 2014/0034545 | A1 | * | 2/2014 | Pawlowski et al. ........... 206/565 |

FOREIGN PATENT DOCUMENTS

| | | |
|---|---|---|
| DE | 10330700 | 1/2005 |
| DE | 102004035061 | 2/2006 |
| WO | 2009130112 | 10/2009 |

\* cited by examiner

DEVICE FOR FILLING AND SEALING PHARMACEUTICAL CONTAINERS

BACKGROUND OF THE INVENTION

The invention relates to a device for filling and sealing pharmaceutical containers.

A device of this type is already commonly known and is used in the pharmaceutical industry to fill and seal syringe barrels. The syringe barrels are here disposed in a carrier element (a so-called nest), the carrier element being in turn disposed in a receptacle (a so-called tub). Such an arrangement of the syringe barrels has the advantage that the syringe barrels can already be presterilized at the site of the glass or plastics manufacturer, so that they have merely yet to be filled and sealed by the druggist.

Apart from the aforementioned syringe barrels, pharmaceutical containers in the form of so-called vials and cartridges, which, in contrast to syringe barrels, are provided with an additional sealing element in the form of a crimp cap, are additionally known. With the previously known device for filling and sealing pharmaceutical containers in the aforesaid carrier elements, a processing or handling of all three aforementioned containers on one and the same device is not possible.

SUMMARY OF THE INVENTION

Starting from the represented prior art, the object of the invention is to refine a device for filling and sealing pharmaceutical containers such that this is suitable also for the handling or for the filling and sealing of pharmaceutical containers to be provided with crimp caps, in particular for vials and cartridges. This object is achieved in a device for filling and sealing pharmaceutical containers. The invention is founded on the idea of assigning to the second handling device a crimping device, which, in dependence on the container which is respectively to be processed, can be controlled by means of the second handling device.

In order to enable a flexible design of the cycle times and of the configuration of the crimping device, in an advantageous refinement it is provided that a feed device having receiving elements for the containers is placed upstream of the crimping device, and in that the receiving elements of the feed device have a take-up region for the containers from the carrier element and a delivery region for the containers to the carrier element, in which the receiving elements, during the delivery or take-up of the containers by means of the second handling unit, are moved past one another together with the second handling unit. It hence becomes possible, for example, for the take-up or delivery of the containers to be realized during a movement of one carrier element, while another carrier element is at the same time present in the crimping device and is motionless there.

In particular it is here advantageous if the second handling unit is configured as a handling robot, whose gripper arm arranged in operative connection with the containers is freely programmable in the horizontal and vertical directions with respect to its motional path. Hence, not only is the device according to the invention fundamentally able to be adapted with respect to the type of containers to be processed, but it is also possible, moreover, given one and the same type of container, to be able to adapt easily to different container formats.

In order to ensure that the chance of losing a crimp cap is as low as possible and that the crimp caps are conveyed over as short a distance as possible within the device, it is additionally advantageous that a crimp cap delivery device, in which the containers respectively take up a crimp cap, is placed directly upstream of the crimping device.

In an alternative embodiment, which is particularly advantageous with respect to the disturbance of the laminar flow within the housing, it is provided, however, that the gripper arm, prior to the removal of the containers on the carrier element, is guided past a crimp cap supplying device, in which the gripper arm removes crimp caps, and that the gripper arm, prior to the removal of the containers from the carrier element, places a crimp cap onto the head region of each container. Since the gripper arm, in the removal of the containers from the carrier element, must in any event be brought into line with the containers, no impairment of the laminar flow ensues from the simultaneous delivery of the caps to the containers.

It is here particularly advantageous if the gripper arm, when the crimp cap is placed onto the container, brings the crimp cap, through crimping on opposite sides, into operative connection with the container, so that the crimp cap is secured on the container. This avoids a situation in which, following the removal of the containers from the carrier element, the crimp cap gets lost between the removal of the containers and the crimping device.

A pharmaceutically secure operation, which, moreover, requires no structural modifications whatever to existing factory buildings, is obtained if the device, with the exception of a feed-in gate and a feed-out gate, is accommodated in a closed housing, and if a blower device is provided, which blower device generates within the housing a laminar flow directed from the ceiling region into the floor region.

In order to enable adaptation to a wide variety of container formats and, fundamentally, also to different containers, it is additionally particularly advantageous that at least the filling and sealing device, the crimping device and the devices assigned to the crimping device are exchangeably fastened to standardized receiving elements.

In order to enable a construction of the device which is as compact as possible, as well as a neat arrangement and good laminar flow, it is additionally advantageous that the conveyor for the receiving container is of rectilinear configuration and extends between the feed-in gate and the feed-out gate in the housing, and that at least the handling devices, the filling and sealing device and the crimping device, as well as the devices assigned to the crimping device, are disposed alongside the conveyor on a common side within the housing.

A configuration in which the first handling device is configured as a handling robot, whose gripper arm arranged in operative connection with the containers is freely programmable in the horizontal and vertical directions with respect to its motional path, and in which, in the motional path of the gripper arm, at least one weighing device for the containers is arranged, yields the advantage that a checking of the containers with respect to the fill quantity becomes possible and the handling device can be easily adapted to different containers.

BRIEF DESCRIPTION OF THE DRAWINGS

Further advantages, features and details of the invention emerge from the following description of preferred illustrative embodiments and with reference to the drawings, in which.

DETAILED DESCRIPTION

Figure 1:
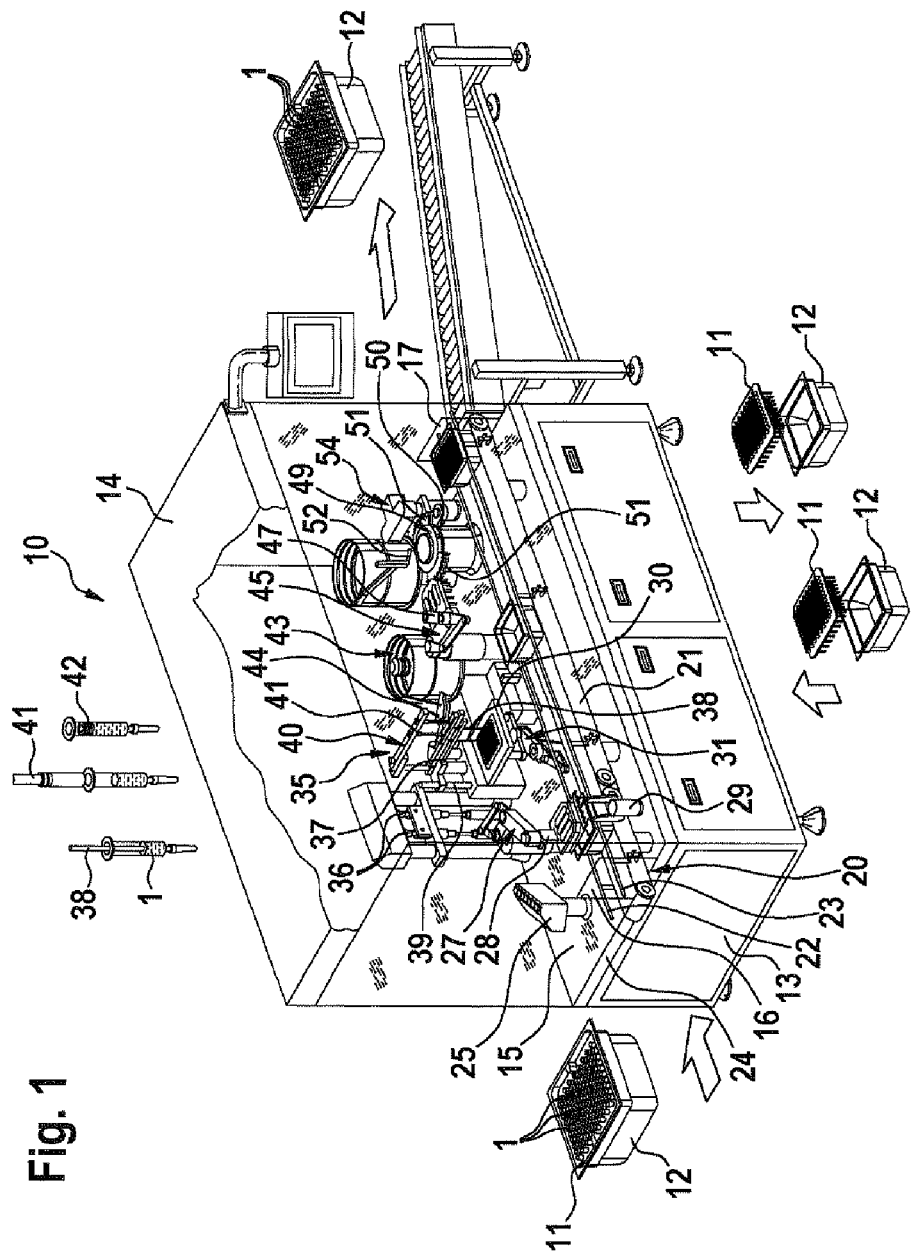
FIG. 1 shows an inventive device for filling and sealing pharmaceutical containers in the processing of syringe barrels, in a partially cut-open perspective representation.
Figure 2:
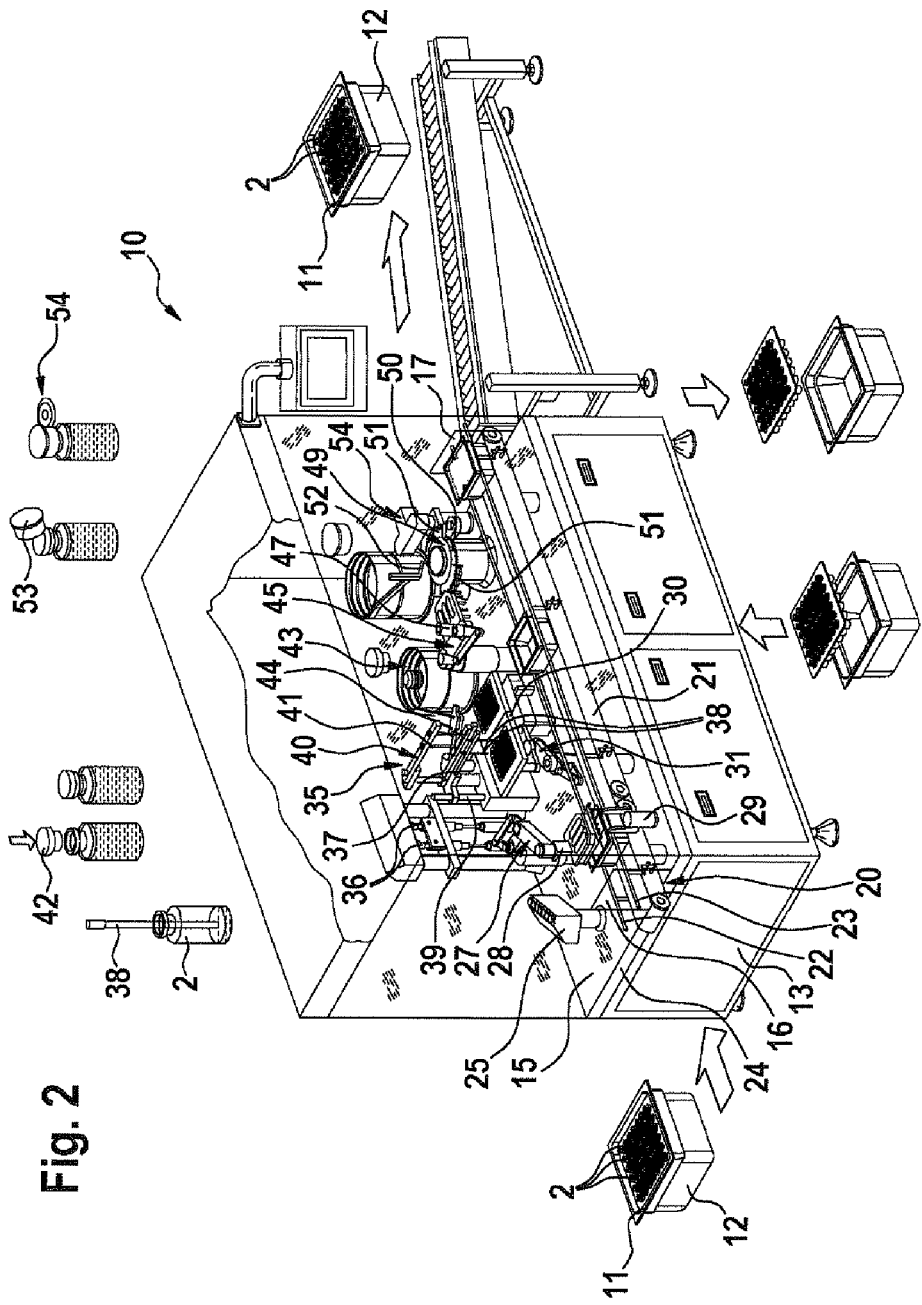
FIG. 2 shows the device according to FIG. 1 during the processing of vials, in a partially cut-open perspective representation.
Figure 3:
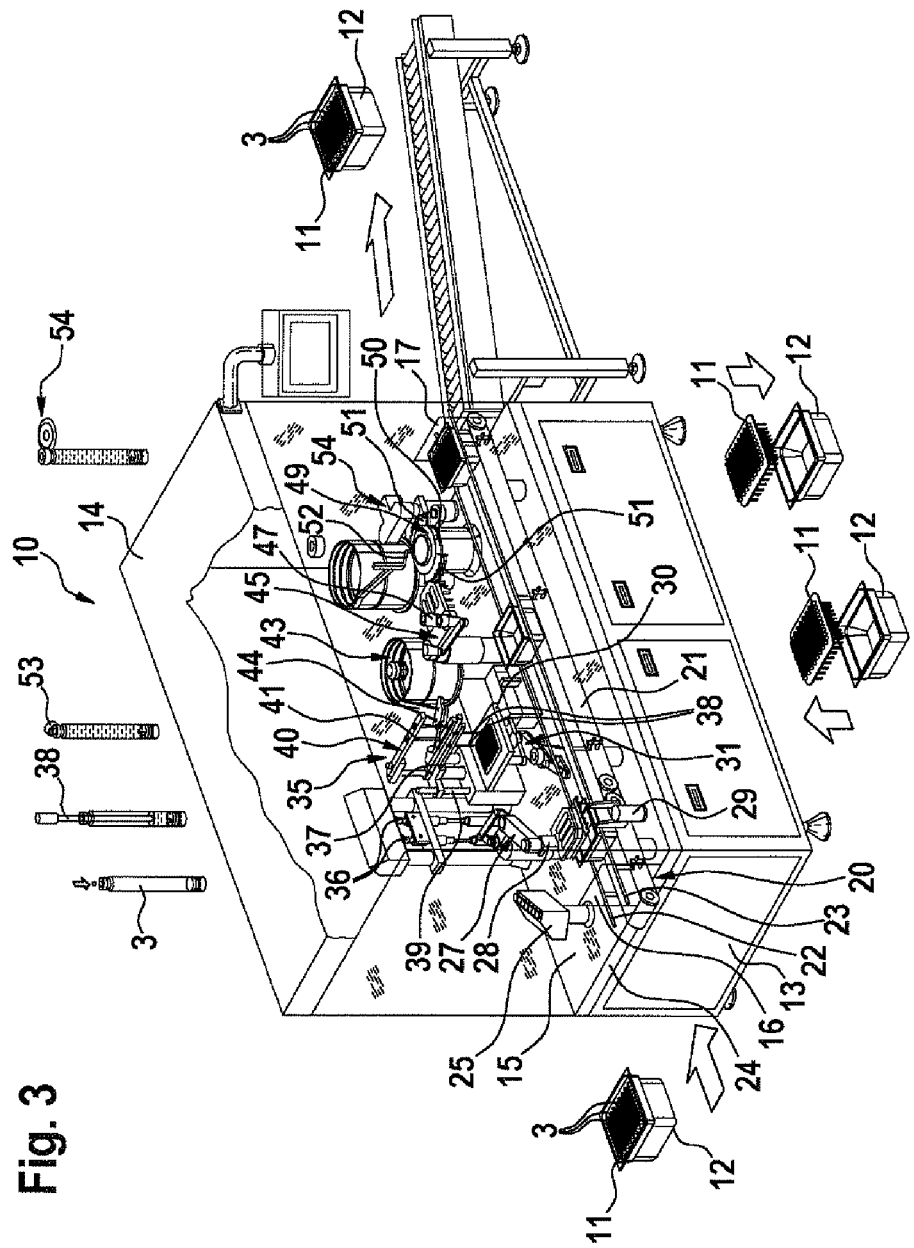
FIG. 3 shows the device according to FIGS. 1 and 2 during the processing of cartridges, likewise in partially cut-open perspective view.

In the figures, identical components are provided with the same reference numerals. That device 10 for filling and sealing pharmaceutical containers which is represented in the figures is suitable for filling and sealing both syringe barrels 1, and vials 2 and cartridges 3. The syringe barrels 1, vials 2 or cartridges 3 are here respectively fed to the device 10 in an at least substantially plate-like receiving element 11 provided with receiving fixtures, the receiving element 11 being inserted in a tub-shaped receptacle 12 and being positioned there by form closure. The receptacle 12 can be sealed by means of a cover (not represented), which serves for protection during transport. This configuration has the advantage that the syringe barrels 1, vials 2 or cartridges 3 can already be (pre)sterilized at the site of the manufacturer of the pharmaceutical containers, so that they have merely yet to be filled and sealed by the druggist.

The device 10 has a box-like housing 13, in whose interior a laminar flow (not represented) directed from the ceiling region 14 in the direction of the floor region 15 of the housing 13 can be generated by means of a blower device. On one end face of the housing 13, a feed-in gate 16 for the receptacles 12 is arranged and, on the opposite-situated end face of the housing 13 there is a feed-out gate 17 for the receptacles 12. Within the housing 13, on its one longitudinal side between the feed-in gate 16 and the feed-out gate 17, a conveyor 20 for the receptacles 12 is found.

In the illustrative embodiment, the conveyor 20 consists of a conveyor belt 21 and two guide rails 22, 23, which guide the receptacles 12 laterally during their transport through the device 10. The rectilinearly configured conveyor 20 is located, as already explained, on one side within the housing 13. On a table leaf 24 in the housing 13, on the other side of the housing 13, handling devices for the containers are disposed. Thus close to the feed-in gate 16 can be seen a weighing device 25, which enables a plurality of pharmaceutical containers to be weighed simultaneously. The weighing device 25 is adjoined by a handling device in the form of handling robot 27, by whose gripper arm 28, in conjunction with a holding device 29, the receiving element 11, together with the pharmaceutical containers disposed therein, can be removed from the receptacle 12 and the receiving element 11 deposited on a transport plate 30.

The transport plate 30 is part of a further transport device 31, which moves the receiving element 11 continuously or cyclically. The handling robot 27 is adjoined by a filling and sealing device 35. The filling and sealing device 35 comprises a plurality of feed pumps 36, by means of which drugs can accurately be metered out on the basis of weight or volume. The feed pumps 36 are connected to a raisable and lowerable filling needle holder 37. On the filling needle holder 37 there is arranged for each container, for example, a filling needle 38.

Upstream of the filling needle holder 37, furthermore, there is optionally placed a first setting tube 39, which can introduce a specific number of balls into each container in order to produce a better mixing of the drugs prior to their administration.

The filling needle holder 37 is adjoined by a gallows-like sealing device 40 for syringe barrels 1. The sealing device 40 comprises for each syringe barrel 1 a second setting tube 41, via which a sealing plug 42 can be inserted into the syringe barrel 1.

Also of fundamental importance is that the handling robot 27 or the motional path of its gripper arm 28 reaches into the region of the filling and sealing device 35, so that the handling robot 27, by means of its gripper arm 28, is able to remove not only unfilled containers from the receiving element 11, but also already filled containers, so as to feed these to the weighing device 25.

In order to supply the sealing plugs 42 or feed them to the setting tubes 39, a sealing plug bin 43, which is coupled via longitudinal conveying units 44 to the setting tubes 39, is additionally provided.

In the region of the sealing plug bin 43, a further handling device in the form of a second handling robot 45 is additionally arranged. The handling robot 45 has a gripper arm 47, by which, according to the nature of a format part mounted on the gripper arm 47, either the syringe barrels 1 arranged side by side and one behind the other in rows in the receiving element 11 and previously filled in the filling and sealing device 35 can be removed and reinserted in the receptacle 12, or else, in the handling of vials 2 or cartridges 3, a specific number of vials 2 or cartridges 3 can be delivered to a downstream feed conveyor 49.

The feed conveyor 49 has a feed wheel 50 having receiving segments 51 arranged movably thereon on its periphery. By means of the receiving segments 51, which rotate during the take-up of vials 2 or cartridges 3, the vials 2 or cartridges 3 are fed past beneath a cap extractor 52 forming part of a crimp cap supply device, whereupon the vials 2 or the cartridges 3, as the vials 2 or the cartridges 3 are fed past, respectively remove or extract a crimp cap 53 from the cap extractor 52.

In one variant (not represented), it is also conceivable, however, that the gripper arm 47 of the handling robot 45 removes an appropriate number of crimp caps 53 from a supply station for the crimp caps 53 and, prior to the removal of the vials 2 or cartridges 3 from the receiving element 11, places the crimp caps 53 onto the vials 2 or cartridges 3 and crimps these on mutually opposing sides.

During the onward movement of the receiving segments 51 on the feed wheel 50, the vials 2 or cartridges 3 make their way into the region of a crimping station 54, at which the crimp caps 53 are crimped onto the vials 2 or cartridges 3. The receiving segment 51 is then moved back to a delivery position corresponding to the take-up position in which the handling robot 45 has transferred the vials 2 or the cartridges 3 into the receiving segments 51.

The device 10 which has so far been described operates as follows: In the processing of syringe barrels 1, the receiving element 11 is removed from the receptacle 12 by means of the handling robot 27 and deposited onto the transport plate 30. After this, it can optionally be provided to remove a specific number of syringe barrels 1 from the receiving element 11 and weigh them on the weighing device 25 prior to being filled. Next, the syringe barrels 1 are filled with a defined fill quantity of drugs, on their path of conveyance in the transport device 31, by means of the filling and sealing device 35. It can then be provided to return the previously weighed, filled syringe barrels 1 by means of the handling robot 27 to the weighing device 25, to check whether the correct fill quantity has been fed in. Next, the sealing plugs 42 are introduced into the syringe barrels 1 and the receiving element 11 is moved by means of the second handling robot 45 back into the receptacle 12. The latter is then discharged from the housing 13 or the device 10 by means of the conveyor 20.

The processing of vials 2 in place of syringe barrels 1 differs from the previously described handling of syringe barrels 1 in that the second handling robot 45 removes the previously filled vials 2, likewise provided with sealing plugs 42, after they have been filled and sealed with the sealing plugs 42, row by row or in batches from the receiving element 11 and delivers them to a receiving segment 51 of the feed wheel 50. Next, the vials 2 are crimped by means of the crimping station 54. Then the second handling robot 45 removes the crimped vials 2 again from the receiving segment 51, in its original position, and inserts the vials 2 into the corresponding receiving fixtures of the receiving element 11. As soon as all the vials 2 from a receiving element 11 are fully crimped, the receiving element 11 is inserted by means of the handling robot 45 back into the receptacle 12 and then discharged from the device 10 by means of the conveyor 20.

The processing of cartridges 3 in place of vials 2 differs from the previously described treatment of the vials 2 particularly in that, in the case of the cartridges 3, no sealing plugs are previously put in place. To this extent, it is particularly important that the laminar flow in the device 10, following the filling of the cartridges 3, is disturbed as little as possible, or that a shortest possible path of conveyance of the cartridges 3 with crimp caps 53 is provided in order to minimize the risk of the crimp caps 53 falling down, so that either the crimp caps 53 on the cap extractor 52 are only extracted immediately prior to the crimping, or, instead. the second handling robot 45, as the cartridges 3 are removed from the receiving element 11, already provides the cartridges 3 with the crimp caps 53, as previously described.

The device 10 which has so far been described can be altered or modified in a variety of ways. For instance, it is conceivable to remove the vials 2 or cartridges 3 by means of the second handling robot 45 directly after filling and to convey them to the receiving segment 51. It is also conceivable to insert the receiving element 11 back into the receptacle 12 after filling and to remove the receiving element 11 from the receptacle 12 again only in the region of a crimping device. In addition, the transfer of the containers from the second handling robot to the receiving segments 51, and vice versa, can take place also in a motionless phase of the receiving segments 51.

The invention claimed is:

1. A device (10) for filling and sealing pharmaceutical containers, wherein the containers are accommodated in a receptacle (12), in which is inserted a carrier element (11) which is removable from the receptacle (12) and in which the containers are arranged side by side and one behind the other in multiple rows in receiving fixtures of the carrier element (11), said device comprising a first handling unit (27) for removing the carrier element (11) from the receptacle (12), a filling and sealing device (35) for the containers, and a second handling unit (45) for reinserting the carrier element (11) into the receptacle (12), which receptacle (12) is transported along with the carrier element (11) on a conveyor (20), characterized in that the containers are configured as syringe barrels (1) or as containers (2, 3) to be provided with crimp caps (53), and in that to the second handling unit (45) there is assigned a crimping device (54), which, in the handling of containers (2, 3) to be provided with crimp caps (53), is controlled by the second handling unit (45), so that the second handling unit (45) first feeds the containers (2, 3) to be provided with crimp caps (53) to the crimping device (54) and then inserts the containers (2, 3) which have been sealed by means of the crimping device (54) back into the carrier element (11).

2. The device as claimed in claim 1, characterized in that a feed device (49) having receiving elements (51) for the containers is placed upstream of the crimping device (54), and in that the receiving elements (51) of the feed device (49) have a take-up region for the containers from the carrier element (11) and a delivery region for the containers to the carrier element (11), in which the receiving elements (51), during the delivery or take-up of the containers by means of the second handling unit (45), are moved past one another together with the second handling unit (45).

3. The device as claimed in claim 1, characterized in that at least the second handling unit is configured as a handling robot (45) having a gripper arm (47) arranged in operative connection with the containers and that is freely programmable in horizontal and vertical directions with respect to a motional path.

4. The device as claimed in claim 1, characterized in that a crimp cap delivery device (52), in which the containers respectively take up a crimp cap (53), is placed directly upstream of the crimping device (54).

5. The device as claimed in claim 3, characterized in that the gripper arm (47), prior to the removal of the containers from the carrier element (11), is guided past a crimp cap supplying device, in which the gripper arm (47) removes crimp caps (53), and in that the gripper arm (47), prior to the removal of the containers from the carrier element (11), places a crimp cap (53) onto a head region of each container.

6. The device as claimed in claim 5, characterized in that the gripper arm (47), when the crimp cap (53) is placed onto the container, brings the crimp cap (53) into operative connection with the container, so that the crimp cap (53) is precrimped onto the container.

7. The device as claimed in claim 1, characterized in that the device (10) is accommodated in a housing (13) that is closed, with the exception of a feed-in gate (16) and a feed-out gate (17), and in that a blower device is provided, which generates within the housing (13) a laminar flow directed from a ceiling region (14) in the direction of a floor region (15) of the housing (13).

8. The device as claimed in claim 1, characterized in that at least one of the filling and sealing device (35), the crimping device (54) and any devices assigned to the crimping device (54), a transport plate (30), and gripper arms (28, 47) of the handling units (27, 45), are exchangeably fastened to standardized receiving elements.

9. The device as claimed in claim 7, characterized in that the conveyor (20) for the receptacle (12) is of rectilinear configuration and extends between the feed-in gate (16) and the feed-out gate (17) in the housing (13), and in that at least the handling units (27, 45), the filling and sealing device (35) and the crimping device (54), as well as any devices assigned to the crimping device, are disposed alongside the conveyor (20) on a common side within the housing (13).

10. The device as claimed in claim 1, characterized in that the first handling unit is configured as a handling robot (27) having a gripper arm (28) arranged in operative connection with the containers and that is freely programmable in horizontal and vertical directions with respect to a motional path, and in that, in the motional path of the gripper arm (28), at least one weighing device (25) for the containers is arranged.

11. The device as claimed in claim 1, characterized in that the receptacle is tub-shaped.

12. The device as claimed in claim 1, characterized in that the containers (2, 3) to be provided with crimp caps (53) are at least one of vials (2) and cartridges (3).

* * * * *